US008921422B2

(12) United States Patent
Kelley

(10) Patent No.: US 8,921,422 B2
(45) Date of Patent: *Dec. 30, 2014

(54) METHODS AND KITS FOR ENHANCING ABILITY TO LEARN IN A PUPPY OR KITTEN

(75) Inventor: Russell Lee Kelley, Eaton, OH (US)

(73) Assignee: The Iams Company, Mason, OH (US)

(*) Notice: Subject to any disclaimer, the term of this patent is extended or adjusted under 35 U.S.C. 154(b) by 750 days.

This patent is subject to a terminal disclaimer.

(21) Appl. No.: 10/945,365

(22) Filed: Sep. 20, 2004

(65) Prior Publication Data

US 2005/0075399 A1    Apr. 7, 2005

Related U.S. Application Data

(60) Provisional application No. 60/507,881, filed on Oct. 1, 2003.

(51) Int. Cl.
*A01N 37/00* (2006.01)
*A61K 47/00* (2006.01)
*A23K 1/18* (2006.01)
*A23K 1/16* (2006.01)

(52) U.S. Cl.
CPC ............. *A23K 1/1893* (2013.01); *A23K 1/1846* (2013.01); *A23K 1/164* (2013.01)
USPC .......................................... 514/560; 424/439

(58) Field of Classification Search
USPC ........................................................ 514/560
See application file for complete search history.

(56) References Cited

U.S. PATENT DOCUMENTS

| | | | |
|---|---|---|---|
| 5,756,088 A | 5/1998 | Matsuura et al. | |
| 5,874,470 A | 2/1999 | Nehne et al. | |
| 6,156,355 A | 12/2000 | Shields, Jr. et al. | |
| 6,245,379 B1* | 6/2001 | Lepine ......................... | 426/656 |
| 6,297,280 B1 | 10/2001 | Ishihara et al. | |
| 6,592,863 B2 | 7/2003 | Fuchs et al. | |
| 6,596,766 B1 | 7/2003 | Igarashi et al. | |
| 6,737,078 B1 | 5/2004 | Kelley | |
| 2002/0077362 A1* | 6/2002 | Lee et al. ...................... | 514/560 |
| 2003/0161864 A1* | 8/2003 | Tanaka et al. ................. | 424/439 |
| 2003/0194478 A1 | 10/2003 | Davenport et al. | |
| 2004/0018224 A1 | 1/2004 | Pierce et al. | |
| 2004/0068010 A1 | 4/2004 | Zicker et al. | |
| 2004/0151761 A1* | 8/2004 | Chew et al. ................... | 424/442 |
| 2005/0032897 A1* | 2/2005 | Kelley .......................... | 514/560 |

FOREIGN PATENT DOCUMENTS

| | | |
|---|---|---|
| DE | 100 47 563 A1 | 9/2000 |
| EP | 0 678 247 A1 | 4/1994 |
| EP | 1 350 435 A2 | 5/2002 |
| JP | 1215245 A | 2/1988 |
| JP | 06319465 A | 5/1993 |
| JP | 08070786 A | 9/1994 |
| JP | 06-319465 | 11/1994 |
| JP | 08-070786 | 3/1996 |
| JP | 8098658 A2 | 4/1996 |
| JP | 10084881 A | 9/1996 |
| JP | 10127257 A | 10/1996 |
| JP | 11071274 A | 8/1997 |
| JP | 10 084881 A | 4/1998 |
| JP | 2002058435 A2 | 5/2002 |
| JP | 2003261456 A2 | 9/2003 |
| WO | WO 00/18247 | 4/2000 |
| WO | WO 00/18247 A1 | 6/2000 |
| WO | WO 01/37678 A1 | 5/2001 |
| WO | WO 02/092540 A1 | 11/2002 |
| WO | WO 2004/006688 A1 | 1/2004 |
| WO | WO 2004/037010 A1 | 5/2004 |
| WO | WO 2005/006877 A1 | 1/2005 |

OTHER PUBLICATIONS

Care of the Pregnant Dog, Jun. 9, 2003, www.marvistavet.com, pp. 1-4.*
Waldron et al., Role of long-chain polyunsaturated n-3 fatty acids in the development of the nervous system of dogs and cats, 1998, JAVMA, 213(5), pp. 619-622.*
Lim et al. (J. Nutr. 130: 1629-1632, 2000, Intakes of Dietary Docosahexaenoic Acid Ethyl Ester and Egg Phosphatidylcholine Improve Maze-Learning Ability in Young and Old Mice).*
Hayek et al., "Utilization of 3 Fatty Acids in Companion Animal Nutrition", *World Rev. Nutr. Diet. Basel Karger*, 1998, vol. 83, pp. 176-185.
Maruha Corp, "*Agents for Improving Smelling and Intellectual Power of Dogs—Contains Glyceride and/or Alkyl Ester of Docosahexaenoic Acid, Used As Food Additive for Police Dogs*", Mar. 19, 1996 (Section Ch, Week 199621, Derwent Publications Ltd., London, GB; Class B05, AN 1996-203073 XP002306961.
Waldron, et al., "*Role of Long-Chain Polyunsaturated n-3 Fatty Acids in the Development of the Nervous System of Dogs and Cata*", JAVMA, vol. 213, No. 5, Sep. 1, 1998.
Pawlosky et al., "*Retinal and Brain Accretion of Long-Chain Polyunsaturated Fatty Acids in Developing Felines: The Effects of Corn Oil-Based Maternal Diets*", Am. J. Clin. Nutri 1997; 65: 465-72.
Yokota, "Relationship Polyunsaturated Fatty Acid (PUFA) and Learning Ability in the Brain of Rat Fetus and Newborn", ACTA Obest Jpn, 1993, 45(1), p. 15-22.
Horrocks et al., "Health Benefits of Docosahexaenoic Acid (DHA)", Pharmacological Research, vol. 40, No. 3, 1999, Abstract.

(Continued)

*Primary Examiner* — Snigdha Maewall
(74) *Attorney, Agent, or Firm* — Christopher D. Brandt; Tracey S. Truitt

(57) ABSTRACT

Processes for enhancing ability to learn in a puppy or kitten comprising orally administering to the puppy or kitten a composition comprising an essential fatty acid component comprising a therapeutically effective amount of docosahexaenoic acid. Processes for enhancing ability to learn in a puppy or kitten comprising orally administering to a respective maternal animal a composition comprising an essential fatty acid component comprising a therapeutically effective amount of docosahexaenoic acid during gestation, nursing, or weaning of the puppy or kitten. Kits comprising a composition comprising an essential fatty acid component comprising a therapeutically effective amount of docosahexaenoic acid; and information that use of the composition will enhance ability to learn in a puppy or kitten.

33 Claims, 2 Drawing Sheets

(56) References Cited

OTHER PUBLICATIONS

Connor et al., "Dietary Effects on Brain Fatty Acid Composition: The Reversibiity of n-3 Fatty Acid Deficiency and Turnover of Docosahexaenoic Acid in the Brain, Erythrocytes, and Plasma of Rhesus Monkeys", Journal of Lipid Research, vol. 31, pp. 237-247, 1990.

De la Presa et al., "Docosahexaenoic and Arachidonic Acid Prevent a Decrease in Dopaminergic and Serotoninergic Neurotransmitters in Frontal Cortex Caused by a Linoleic and Alpha-Linolenic Acid Deficient Diet in Formula-fed Piglets", The Journal of Nutrition, pp. 2088-2093, Jul. 5, 1999.

Gamoh et al., "Chronic Administration of Docosahexaenoic Acid Improves Reference Memory-Related Learning Ability in Young Rats", Neuroscience, vol. 93, No. 1, 1999, Abstract.

Moriguchi et al., "Recovery of Brain Docosahexaenoate Leads to Recovery of Spatial Task Performance", Journal of Neurochemistry, No. 87, pp. 297-309, 2003.

Takeuchi et al., "Influence of a Dietary n-3 Fatty Acid Deficiency on the Cerebral Catecholamine Contents, EEG and Learning Ability in a Rat", Behavioural Brain Research, No. 131, 2002.

Pawlosky et al., "Retinal and brain accretion of long-chain polyunsaturated fatty acids in developing felines: the effects of corn oil-based maternal diets", Am J Clin Nutr., vol. 65, No. 2, pp. 465-472, 1997.

Krabbendam et al., LCPUFA's and Maternal and Child Health Workshop, May 21, 2008.

Donadio, James and Joseph Grande, "The Role of Fish Oil/Omega-3 Fatty Acids in the treatment of IgA nephropathy", J Am Soc Nephrol, vol. 10, pp. 1772-1777, 1999.

\* cited by examiner

US 8,921,422 B2

METHODS AND KITS FOR ENHANCING ABILITY TO LEARN IN A PUPPY OR KITTEN

CROSS REFERENCE TO RELATED APPLICATION

This claims the benefit of U.S. Provisional Application 60/507,881, filed Oct. 1, 2003.

FIELD OF THE INVENTION

The present invention is directed to methods or kits that are useful for enhancing ability to learn in a puppy or kitten. The methods and kits utilize a composition comprising an essential fatty acid component comprising a therapeutically effective amount of DHA in an orally administrable composition such as a supplement or food.

BACKGROUND OF THE INVENTION

Ability to learn in a puppy or kitten is an important attribute for successful social and physical interaction between the animal and human, such as an owner or other guardian. For example, this is particularly important in the training of future working dogs, such as police dogs, hunting dogs, or service dogs, but may be equally important for successful socialization of the typical companion animal. However, training puppies or kittens in this regard has proven difficult and often requires extensive intervention, such as obedience schools and other formal trainings. Even with such formal trainings, the puppy or kitten may not be successfully trained or have the capacity to successfully learn expected tasks. Moreover, brain development and cognitive function may not develop successfully despite measures to train the animal.

As such both puppies and kittens are in need of measures which can enhance their brain development, cognitive function, or ability to learn or train.

Omega-3-fatty acids and omega-6-fatty acids are components which have recently become interesting to researchers for a variety of reasons. For example, these components have been shown to provide a variety of beneficial results in the human species, for example, in terms of cardiac or skin health. Moreover, cognitive function in humans ingesting enriched meat sources of docosahexaenoic and eicosapentaenoic acids has been disclosed. However, it appears that the cognitive effects of these fatty acids have not been extensively studied in animals such as dogs or cats.

Ishihara et al. have reported that theanine can assist with the suppression of behavior problems in dogs and cats, which may optionally be used in combination with highly unsaturated fatty acids. Ishihara et al. do not speculate regarding the efficacy of such fatty acids in the absence of theanine, nor is there any indication that there is any effect of theanine beyond suppression of unfavorable behavior. See U.S. Pat. No. 6,297,280. Moreover, puppies, regardless of birth status, are not studied. See JP 8070786.

However, certain uses of omega-3-fatty acids and omega-6-fatty acids have been studied in companion animals. The present inventor has previously reported the surprising effect of omega-3-fatty acids and omega-6-fatty acids in the reproductive performance of canines and felines. In such report, the inventor has described that upon feeding the diet containing the omega-3-fatty acids and omega-6-fatty acids, the essential fatty acid status in the maternal animal is maintained and litter size is maintained through subsequent parities. In contrast, when the maternal animal is not fed diets containing the enriched sources of omega-3-fatty acids and omega-6-fatty acids, the essential fatty acid status in subsequent parities decreases, which decreases overall reproductive performance and live birth successes. See WO 01/37678.

Further extensive studies conducted by the present inventor have resulted in the present invention described herein. In particular, the present inventor has discovered processes of enhancing ability to learn in a puppy or kitten, which processes utilize a composition comprising a therapeutically effective amount of a component selected from the group consisting of omega-3-fatty acids, omega-6-fatty acids, and mixtures thereof. Even further surprisingly, administration may be directly to the puppy or kitten in need of treatment, or directly to the respective maternal animal with similar results. These and other advantages are described in further detail herein.

SUMMARY OF THE INVENTION

The present invention is directed to processes for enhancing ability to learn in a puppy or kitten comprising orally administering to the puppy or kitten a composition comprising an essential fatty acid component comprising a therapeutically effective amount of DHA.

The invention is further directed to processes for enhancing ability to learn in a puppy or kitten comprising orally administering to a respective maternal animal a composition comprising an essential fatty acid component comprising a therapeutically effective amount of DHA during gestation, nursing, or weaning of the puppy or kitten.

The invention is further directed to kits comprising a composition comprising an essential fatty acid component comprising a therapeutically effective amount of DHA and information that use of the composition will enhance ability to learn in a puppy or kitten.

These and other aspects of the present invention are described in further detail herein.

DETAILED DESCRIPTION OF THE INVENTION

Figure 1:
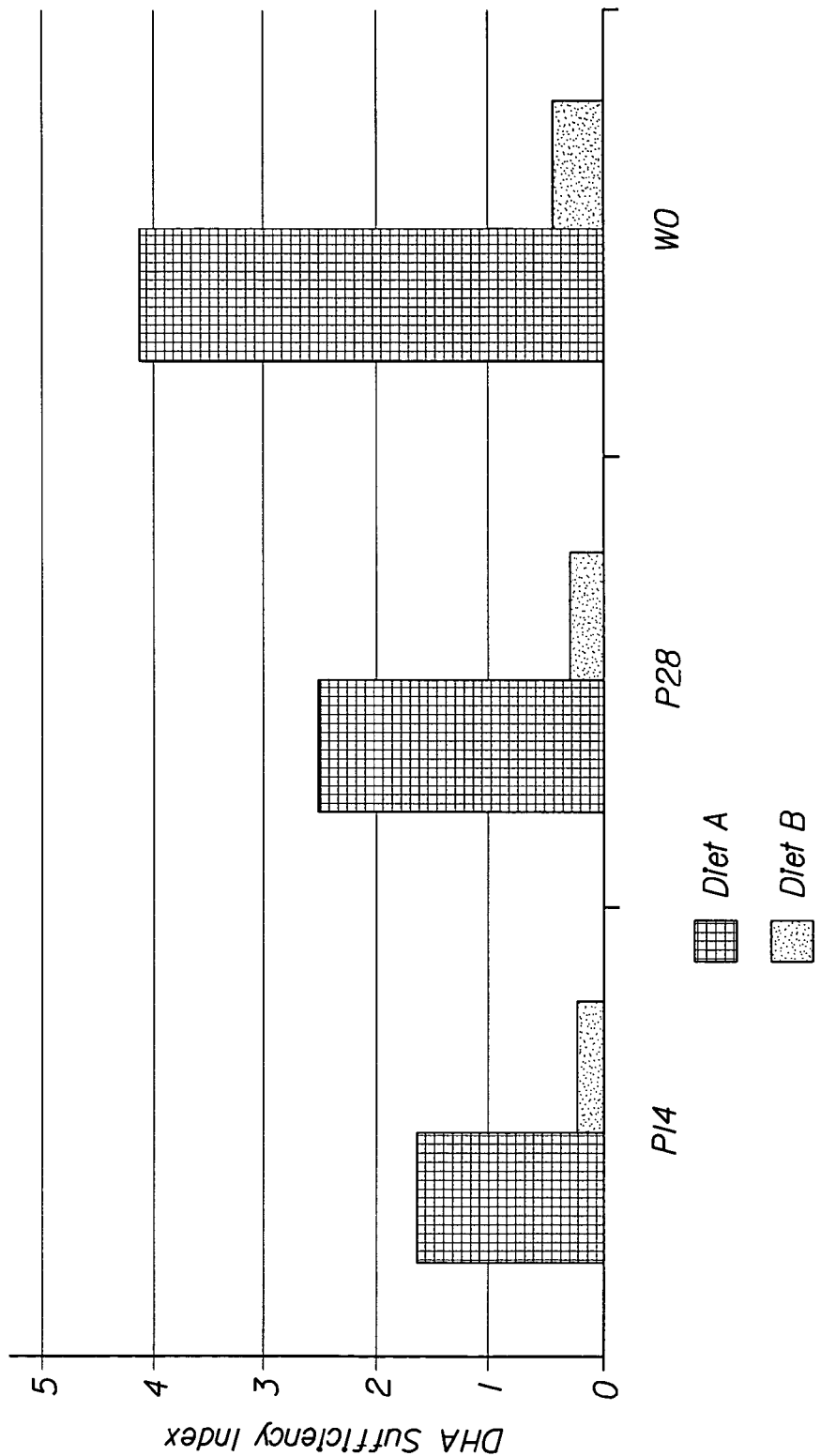
FIG. 1 shows the effect of maternal dietary DHA on the DHA status of the puppies at days 14, 28 and 42 of age (P14, P28 and WO, respectively). See Example 1 herein.

Various documents including, for example, publications and patents, are recited throughout this disclosure. All such documents are hereby incorporated by reference.

All percentages and ratios are calculated by weight unless otherwise indicated. All percentages and ratios are calculated based on the total composition unless otherwise indicated.

Referenced herein are trade names for components including various ingredients utilized in the present invention. The inventors herein do not intend to be limited by materials under a certain trade name. Equivalent materials (e.g., those obtained from a different source under a different name or reference number) to those referenced by trade name may be substituted and utilized in the descriptions herein.

In the description of the invention various embodiments or individual features are disclosed. As will be apparent to the ordinarily skilled practitioner, all combinations of such embodiments and features are possible and can result in preferred executions of the present invention.

The compositions herein may comprise, consist essentially of, or consist of any of the elements as described herein.

While various embodiments and individual features of the present invention have been illustrated and described, various other changes and modifications can be made without departing from the spirit and scope of the invention. As will also be apparent, all combinations of the embodiments and features taught in the foregoing disclosure are possible and can result in preferred executions of the invention.

As used herein, the term "ability to learn" with reference to a given puppy or kitten shall include the following to the extent that the following may be interpreted as differing: ability to learn, ability to train, brain development, cognitive function, and the like. Among the described properties, cognitive function, ability to learn, ability to train, and combinations thereof are particularly interesting as these properties are descriptive of results which are readily observable by the owner of the puppy or kitten.

As used herein, the term "DHA" refers to docosahexaenoic acid.

As used herein, the term "kitten" refers to a domestic feline which is about 3 years old or less, alternately about 2 years old or less, alternately about 1 year old or less, all of which shall include reference to the feline in its gestational state.

As used herein, the term "puppy" refers to a domestic canine which is about 3 years old or less, alternately about 2 years old or less, alternately about 1 year old or less, all of which shall include reference to the canine in its gestational state. Processes directed to ability to learn in puppies are particularly interesting herein.

As used herein, the term "respective maternal animal," with reference to a puppy or kitten, refers to the biological mother of the referenced puppy or kitten (regardless of birth status, i.e. whether the referenced puppy or kitten is still in its gestational state).

The Processes of the Present Invention

The present processes are defined herein in a number of embodiments, all relating to the discoveries made by the present inventor. In particular, the present inventor has previously discovered that the essential fatty acid status of an animal is associated with the reproductive performance of the animal. For example, it has been found that in canines, with each subsequent parity, the essential fatty acid status of the bitch declines due to a depletion of selected omega-3-fatty acids and omega-6-fatty acids. See WO 01/37678.

Among other discoveries herein, it has been found that therapeutically effective DHA supplementation can enhance ability to learn in a puppy or kitten. Further to this discovery, such supplementation can surprisingly be made through oral administration of a composition described herein directly to the puppy or kitten, or to the respective maternal animal during the gestational, nursing, or weaning processes, or any combination thereof, with similarly advantageous results.

Consistent with these discoveries, the present invention relates to various processes for enhancing ability to learn in a puppy or kitten.

In one embodiment, the processes relate to oral administration of a composition described herein directly to a puppy or kitten. In this embodiment, the invention is a process of enhancing ability to learn in a puppy or kitten comprising orally administering to the puppy or kitten a composition comprising an essential fatty acid component comprising a therapeutically effective amount of DHA. In an optional aspect of this embodiment, the compositions are administered during at least weaning of the puppy or kitten from its respective maternal animal. That is, in this optional aspect, the puppy or kitten experiencing weaning is administered the composition, and may optionally be administered the composition subsequent to weaning as well. In another optional aspect of this embodiment, the compositions are administered at least subsequent to weaning. The various embodiments of the composition used in this method, including forms or the composition and levels of various components contained therein, are described in further detail herein below.

In another embodiment of the processes herein, the invention is process for enhancing ability to learn in a puppy or kitten comprising orally administering to a respective maternal animal a composition comprising an essential fatty acid component comprising a therapeutically effective amount of DHA during gestation, nursing, weaning, or any combination thereof, of the puppy or kitten. The various embodiments of the composition used in this method, including forms or the composition and levels of various components contained therein, are described in further detail herein below.

As used herein with respect to the processes of this invention, the terms "orally administering," "oral administration" or the like means that the puppy, kitten, or respective maternal animal, as applicable, ingests or is directed to ingest one or more compositions described herein, or the owner of such puppy, kitten, or respective maternal animal is directed to provide one or more compositions to the puppy, kitten, or respective maternal animal. Wherein the owner is directed to provide, such direction may be that which instructs and/or informs the owner that use of the composition may and/or will provide one or more of the benefits described herein, such as enhancing ability to learn in a puppy or kitten. For example, such direction may be oral direction (e.g., through oral instruction from, for example, a veterinarian, other health professional, sales professional or organization, and/or radio or television media (i.e., advertisement) or written direction (e.g., through written direction from, for example, a veterinarian or other health professional (e.g., scripts), sales professional or organization (e.g., through, for example, marketing brochures, pamphlets, or other instructive paraphernalia), written media (e.g., internet, electronic mail, or other computer-related media), and/or containing devices associated with the composition (e.g., a label present on a package containing the composition).

The compositions may be administered in accordance with a variety of frequencies or durations. For example, wherein the compositions are food compositions, the compositions are typically administered from once daily to about four times daily, alternately from once daily to about three times daily, alternately from once daily to about two times daily, alternately ad libitum. In order to achieve the benefits herein, it is preferred that the compositions are administered for at least about one week, alternatively at least about two weeks, alternately at least about three weeks, alternately at least about four weeks, alternately at least about 6 weeks, alternately at least about eight weeks, or in an unlimited duration. Alternatively or additionally, the compositions are administered during gestation (i.e., administration to the respective maternal animal), during nursing (i.e., administration to the respective maternal animal), during the weaning processes (i.e., administration to the respective maternal animal or the puppies or kittens), subsequent to weaning, or any combination thereof.

The Kits of the Present Invention

The present invention further relates to kits which assist with communicating the benefits of the discoveries made herein to, for example, an animal owner or other guardian or interested individual. In particular, the present kits comprise:

(a) a composition comprising an essential fatty acid component comprising a therapeutically effective amount of DHA; and (b) information that use of the composition will enhance ability to learn in a puppy or kitten.

In accordance with the previously described processes, the compositions utilized in the kits may be intended for use by the puppy, kitten, respective maternal animal, or any combinations thereof.

The kits of the present invention may comprise one or more compositions together with information which informs a user of the kit, or owner, other guardian, or other interested individual, by words, pictures, and/or the like, that use of the kit may and/or will provide enhanced ability to learn. Such information need not utilize the actual words used herein, for example, "brain", "development", "cognitive", "learn", "train", or the like, but rather use of words, pictures, symbols, and the like conveying the same or similar meaning are contemplated within the scope of this invention. The information is preferably consistent with the various embodiments of the processes described herein above.

In a particularly preferred embodiment, the information is printed on a container holding the composition, e.g., a bag, can, carton, pouch, or other container used in the dog (including puppy) or cat (including kitten) food arts. These preferred kits may be in the form of one container containing the composition, or may be obtained as a plurality of containers each containing the composition. For example, the kits may be obtained as one bag, or cases of four, six, eight, or twelve cans or other like containers co-packaged together.

The Compositions Used in Accordance With the Present Invention

The present methods and kits utilize a composition comprising an essential fatty acid component comprising a therapeutically effective amount of DHA. As has been stated, as used herein, the term "DHA" refers to docosahexaenoic acid.

The essential fatty acid component comprises at least DHA, but may optionally comprise one or more other essential fatty acids as well. As used herein, the essential fatty acids include omega-3-fatty acids and omega-6-fatty acids.

DHA is a well-known omega-3-fatty acid. As is well-understood in the art, omega-3-fatty acids are those fatty acid materials having an omega-3 double bond wherein the first double bond in the carbon chain is positioned between the third and fourth carbon atoms of the fatty acid chain, when counting from the omega (distal) carbon atom of the chain.

Omega-3-fatty acids are preferably derived from marine (fish) sources, including menhaden (a herring-like fish) and, as such, may be delivered in the form of such sources. Non-limiting examples of omega-3-fatty acid sources include OMEGAPURE, commercially available from Omega Protein, Inc., Houston, Tex. All forms of the fatty acid are also contemplated herein. For example, DHA is often provided as a triglyceride. As such, wherein a specific fatty acid is mentioned (e.g., "DHA"), such fatty acid includes the free form of the fatty acid as well as other forms such as the naturally occurring triglyceride or other form. The terms, DHA, EPA, or other specific terms are utilized for convenience as will be commonly understood in the art to include all forms of such termed material.

Non-limiting examples of omega-3-fatty acids which are suitable for use herein include eicosapentaenoic acid (also known as EPA) and, of course, the DHA.

Omega-6-fatty acids may be utilized herein. As is well-understood in the art, omega-6-fatty acids are those fatty acid materials having a double bond positioned between the sixth and seventh carbon atoms of the fatty acid chain, when counting from the omega (distal) carbon atom of the chain.

Often the compositions utilized herein will comprise a mixture of omega-3-fatty acids and omega-6-fatty acids, often through utilization of various materials containing these components. Preferred compositions for use herein may be enriched in one or more specific omega-3-fatty acids or omega-6-fatty acids.

The composition may be of any form that is orally administrable. For example, the composition may be a supplement or a food composition. Supplements may include dosage forms such as tablets, capsules, or the like, or other forms such as biscuits, chews, or other treats. Food compositions are readily understood in the art, for example, dry foods, semi-moist foods, and wet foods, all utilized as canine (including puppy) or feline (including kitten) foods.

As used herein, the term "therapeutically effective amount," with reference to the DHA used herein, means that amount of DHA sufficient to provide enhanced ability to learn in a puppy or kitten, whether administered to directly to the puppy or kitten itself or directly to the respective maternal animal. The specific "therapeutically effective amount" will vary with such factors as the physical condition of the puppy or kitten, the age or birth status of the puppy or kitten, the duration of treatment, the nature of concurrent therapy (if any), the specific form of composition to be used, and the like, which will be well understood by one of ordinary skill given the disclosures provided herein.

As another example, wherein the composition is a food composition, the composition may for example comprise, on a dry matter basis, at least about 0.06%, alternatively at least about 0.1%, alternatively at least about 0.12%, alternatively from about 0.1% to about 1%, or alternatively from about 0.1% to about 1% of DHA, by weight of the composition. As another example, food compositions may often comprise, on a dry matter basis, from about 0.1% to about 15%, alternatively from about 0.2% to about 10%, alternatively from about 0.5% to about 9%, alternatively from about 1% to about 9% of essential fatty acids, by weight of the composition.

As another example, supplement compositions such as biscuits, chews, gravies or other treats or supplements, including milks or milk replacers may for example comprise, on a dry matter basis, at least about 0.06%, alternatively at least about 0.1%, alternatively at least about 0.12%, alternatively from about 0.1% to about 75%, or alternatively from about 0.1% to about 1% of DHA, by weight of the composition. As another example, such supplement compositions may often comprise, on a dry matter basis, from about 0.1% to about 75%, alternatively from about 0.2% to about 10%, alternatively from about 0.5% to about 9%, alternatively from about 1% to about 9% of essential fatty acids, by weight of the composition.

Other supplement forms such as tablets, capsules, or the like may often for example comprise higher levels of DHA or essential fatty acids (in terms of percent level by weight of the composition) relative to biscuits, chews, gravies or other treats, including milks or milk replacers, or relative to food compositions.

Other components are beneficial for inclusion in the compositions used herein, but are optional for purposes of the invention. For example, food compositions are preferably nutritionally balanced. Food compositions may, for example, include kibbles, semi-moist, or wet foods, as well as milks and milk replacers (milks and milk replacers, as used herein, may be either foods or supplements). In one embodiment, the food compositions may comprise, on a dry matter basis, from about 20% to about 50% protein, or from about 22% to about 40% protein, by weight of the food composition. As another example, the food compositions may comprise, on a dry matter basis, from about 5% to about 35% fat, or from about 10% to about 30% fat, by weight of the food composition. In another embodiment, supplement compositions such as biscuits, chews, and other treats may comprise, on a dry matter basis, from about 20% to about 50% protein, or from about 22% to about 40% protein, by weight of the supplement composition. As another example, these types of supplement compositions may comprise, on a dry matter basis, from about 5% to about 35% fat, or from about 10% to about 30% fat, by weight of the supplement composition. As yet another example, supplement compositions such as gravies or other food toppings may often comprise from about at least about 0.5% protein, or at least about 0.8% protein, by weight of the supplement composition. As yet another example, supplement compositions such as gravies or other food toppings may often comprise from about at least about 1% fat, or at least about 2% fat, or from about 1% to about 5% fat, by weight of the supplement composition. As yet another example, supplement compositions such as gravies or other food toppings may often comprise from about at least about 50% moisture, or at least about 70% moisture, or from about 70% to about 99% moisture. Food and supplement compositions intended for use by canines or felines are commonly known in the art.

In an optional and not required embodiment herein, the compositions utilized may be substantially free of theanine. As used herein, "substantially free of theanine" means that the compositions comprise less than about 0.06% theanine, or even less than about 0.00025% theanine, by weight of the composition. A discussion of theanine is provided in U.S. Pat. No. 6,297,280.

EXAMPLES

The following examples are provided to illustrate the invention and are not intended to limit the scope thereof in any manner.

Example 1

The effect of maternal animal diet on puppy DHA status is evaluated. Two groups of maternal animals are fed a nutritionally balanced composition. However, one group of maternal animals is fed a nutritionally balanced composition comprising about 0.14% DHA, by weight of the composition ("Diet A"). The other group of maternal animals is fed a nutritionally balanced composition comprising about 0.02% DHA, by weight of the composition ("Diet B"). The maternal animals nurses their respective puppies, and the DHA Sufficiency Index of the puppies is measured at 14 ("P14"), 28 ("P28"), and 42 ("W0") days of age. The DHA Sufficiency Index is the relative ratio between DHA (22:6n-3) and the omega-6-fatty acid known as osbond acid (22:5n-6), as measured via red blood cell membrane. FIG. 1 demonstrates that the DHA Sufficiency Index (as indicated by y-axis of the figure) is significantly higher in the puppies nursing from their respective maternal animal which is fed Diet A relative to the puppies nursing from their respective maternal animal which is fed Diet B. It is therefore concluded that DHA status of puppies nursing from their respective maternal animal consuming a composition containing about 0.14% DHA is significantly higher than that of puppies nursing from their respective maternal animal consuming a composition containing about 0.02% DHA, and this effect is enhanced significantly through duration of nursing.

Example 2

A study is conducted to determine effect of compositions described herein upon the ability of puppies to learn in a training environment.

Ten purebred beagle puppies are randomized and assigned to Group 1 (n=3), Group 2 (n=3), or Group 3 (n=4). Each of the puppies is about nine weeks of age. Their respective weights are appropriate for age and body size.

Three treatment compositions are utilized for the study. These compositions are: 1) for Group 1, a nutritionally balanced food composition comprising an essential fatty acid component comprising about 0.14% DHA, by weight of the composition; 2) for Group 2, a nutritionally balanced food composition which is similar in all respects except that the essential fatty acid component comprises about 0.08% DHA, by weight of the composition; and 3) for Group 3, a nutritionally balanced food composition which is similar in all respects except that the essential fatty acid component comprises about 0.02% DHA, by weight of the composition.

The respective maternal animal for each puppy in Group 1 receives, ad libitum, a nutritionally balanced food composition comprising an essential fatty acid component comprising about 0.14% DHA, by weight of the composition, during gestation, nursing, or weaning (or any combination thereof) of such puppy.

The respective maternal animal for each puppy in Group 2 receives, ad libitum, a nutritionally balanced food composition comprising an essential fatty acid component comprising about 0.08% DHA, by weight of the composition, during gestation, nursing, or weaning (or any combination thereof) of such puppy.

The respective maternal animal for each puppy in Group 3 receives, ad libitum, a nutritionally balanced food composition comprising an essential fatty acid component comprising about 0.02% DHA, by weight of the composition, during gestation, nursing, or weaning (or any combination thereof) of such puppy.

Throughout the study, the puppies are fed their respective compositions twice daily. Treats are utilized for training purposes; the treats which are used are PURINA® Puppy Canned Formula.

Figure 2:
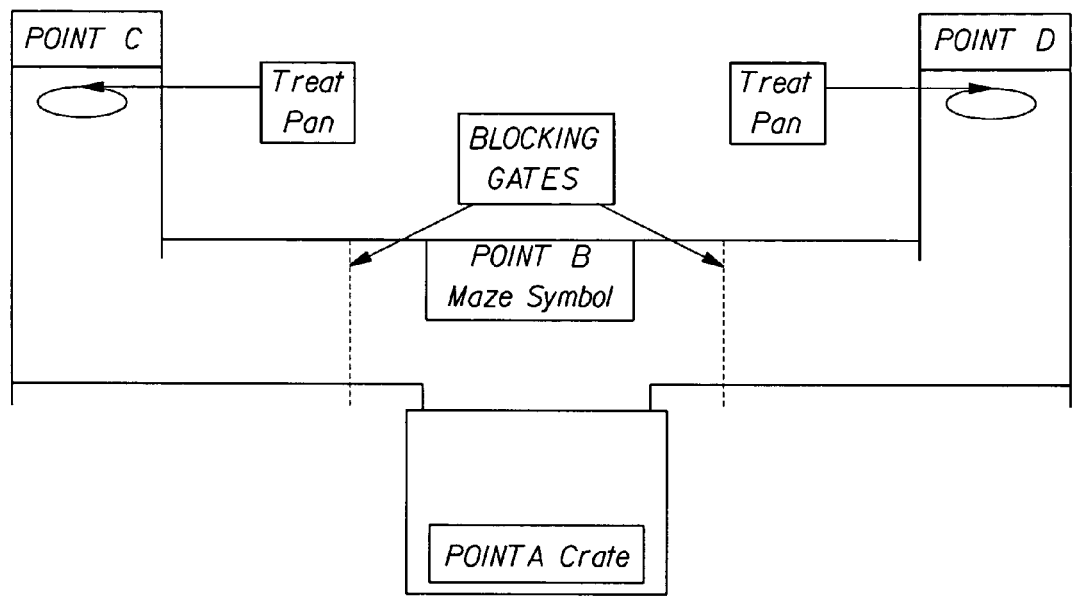
FIG. 2 shows a maze which is herein utilized to test the training ability of puppies fed various diets, including those compositions of the present invention. See Example 2 herein.

The study utilizes a room having a maze constructed in general accordance with the maze illustrated in FIG. 2. Referring now to FIG. 2, Point A Crate is a starting area and contains a crate with a door that cannot be seen through. This crate door is easily opened by a study technician. The crate allows immediate entrance into the maze when the door is opened. The crate door is opened either upward or flat, or by some other means such that the maze path is not obstructed. Point B Maze Symbol contains one of two symbols (i.e., a circle and square) indicating to the trained puppy where the treat will be located. The symbol is attached at a height which is easily visualized by the puppy. Point C Treat Pan is the ending location where the treat pan will be located. Point C Treat Pan is the correct designation for a maze designated left. Point D Treat Pan is the ending location where another treat pan will be located. Point D Treat Pan is the correct designation for a maze designated right.

Prior to training, each puppy is randomly assigned two symbol-direction combinations. The possible groupings are identified below as Groups A and B:

| Group A | Group B |
|---|---|
| Circle - Right (CR) | Circle - Left (CL) |
| Square - Left (SL) | Square - Right (SR) |

Training with assistance takes place for one week. Each puppy is trained in accordance to whether it is a Group A puppy or a Group B puppy. For Group A puppies, the puppy is trained numerous times to learn that if a treat is placed on the circle at Point B Maze Symbol, then another treat is located to the right at Point D Treat Pan. Likewise, for Group A puppies, the puppy is trained the same number of time to learn that if a treat is placed on the square at Point B Maze Symbol, then another treat is located to the left at Point C Treat Pan. Group B puppies will follow this same outline with the exception that sessions with a circle as the symbol will go to the left and a square as the symbol will go right. All puppies are trained the same number of times for each symbol, using learning procedures such as placing a trail of treats in the correct direction.

Following the one-week training period, each puppy enters the daily testing period. During this period each puppy receives three sessions per day (Monday through Friday) with seven trials in each session for a total of twenty-one trials per day.

Each puppy will have a randomized trial order. The starting point for all puppies is Point A Crate. Once a puppy has turned right or left coming out of Point A Crate and passed a point approximately 4 feet to the left or right of the Point B Maze Symbol, that direction is considered the choice and the maze trial is scored either correct or incorrect. Should a puppy proceed in the wrong direction, a blocking gate will prevent it from turning around and reaching the treat. Each puppy is tested until it achieves a success criteria, which is defined as scoring 12 of 14 correct test over two consecutive sessions or 17 of 21 correct test over three consecutive sessions. After achieving a success criteria, a puppy is switched to the opposing group. Testing will continue in this manner until the end of the study period, 25 test days, or a puppy achieves three success criteria.

For Group 1 puppies (composition comprising an essential fatty acid component comprising about 0.14% DHA, by weight of the composition), 100% of the puppies achieved a single success criteria. For Group 1 puppies, 66% of the puppies achieved two success criteria.

For Group 2 puppies (composition comprising an essential fatty acid component comprising about 0.08% DHA, by weight of the composition), 66% of the puppies achieved a single success criteria. For Group 2 puppies, 0% of the puppies achieved two success criteria.

For Group 3 puppies (composition comprising an essential fatty acid component comprising about 0.02% DHA, by weight of the composition), 50% of the puppies achieved a single success criteria. For Group 3 puppies, 0% of the puppies achieved two success criteria.

Example 3

A study is conducted to determine effect of compositions described herein upon the ability of puppies to learn in a training environment.

Twelve purebred beagle puppies are randomized and assigned to either Group 1 or Group 2. Each of Groups 1 and 2 contains six of the puppies. Each of the puppies is about nine weeks of age. Their respective weights are appropriate for age and body size.

Two treatment compositions are utilized for the study. These compositions are: 1) for Group 1, a nutritionally balanced food composition comprising an essential fatty acid component comprising 0.18% DHA, by weight of the composition; and 2) for Group 2, a nutritionally balanced food composition which is similar in all respects except that the essential fatty acid component comprises 0.02% DHA, by weight of the composition.

Throughout the study, the puppies are fed their respective compositions ad libitum. Treats are utilized for training purposes; the treats which are used are PURINA® Puppy Canned Formula.

The study utilizes three doors of identical size and shape. Each puppy is randomly assigned to one of three doors along with a random symbol (circle or square) for location training. The objective of the study is to train the puppy to reach the "correct" door, i.e. the door bearing the shape which is assigned to the respective puppy. A box is marked with tape in front of each door. The puppy must have front paw(s) in the box before the door is opened, revealing the treat. Treats are placed in a manner such to eliminate scent cues. Following training, all puppies are tested to determine their ability to locate an assigned location (door). All puppies, regardless of group, achieved greater than 90% correct scores.

Following location training, each puppy receives two days of shape training, wherein the study shapes are randomly placed on different doors simultaneously. The objective is to determine whether the puppy learns that the symbol is associated with the treat target, not the door location. Following this training, each puppy received two testing sessions to determine ability to identify the symbol as the cue. A puppy is determined to pass if at least 80% of the test is correct. Puppies that failed are given two additional days of training and are retested. A puppy is given a maximum of three attempts to pass the multiple shape testing.

Each puppy is randomly assigned a shape of either a square or a circle. The "correct" door is the door bearing the shape which is assigned to the puppy; the location of the "correct" door is systematically modified throughout the study such that the puppy must learn to identify with the shape rather than the location of the door. The puppies are trained for several days in order to learn the process of choosing the "correct" door within a time period of two minutes. Training occurs with various learning procedures, including placing a trail of treats in front of the "correct" door.

After several days of training, the learning procedures are eliminated and the puppy performs without intervention. The puppy is given two minutes to reach the "correct" door. If the puppy fails to reach the "correct" door within the two minute time period, the puppy receives an incorrect score for that attempt. If the puppy reaches the "correct" door within the two minute time period, the puppy receives a correct score for that attempt.

Overall, 50% of the puppies in Group 1 passed the test on their initial testing compared to only 16% of the puppies in Group 2. Following additional training days, 75% of the Group 1 passed compared to only 45% of the puppies in Group 2.

Example 4

The following dog food composition, in the form of kibbles, is to feed puppies or their respective maternal animals with the objective of achieving the benefits of the present invention: EUKANUBA® Puppy Weaning Diet Formula; EUKANUBA® Puppy Small Breed Formula; EUKANUBA® Puppy Lamb & Rice Formula; EUKANUBA® Premium Performance (including Large Breed) Formula; and EUKANUBA® Premium Performance Formula; EUKANUBA® Kitten Chicken & Rice Formula; all commercially available from The Iams Company, Dayton, Ohio. Guaranteed analyses of such products are publicly available. The compositions may be made according to processes which are known in the art.

What is claimed is:

1. A process for enhancing ability to learn in a puppy or kitten comprising orally administering to a respective maternal animal during weaning of the puppy or kitten a composition comprising:
   a. from about 0.02% to less than about 0.18%, by weight of the composition on a dry matter basis, therapeutically effective docosahexaenoic acid;
   b. an omega-6 fatty acid;
   b. from about 20% to about 50%, by weight of the composition on a dry matter basis, protein; and
   c. from about 5% to about 35%, by weight of the composition on a dry matter basis, fat;
   wherein the composition is a supplement selected from the group consisting of biscuits, chews, gravies, and treats or is a food composition selected from the group consisting of nutritionally balanced kibbles and semi-moist foods.

2. The process according to claim 1 wherein the composition is a supplement composition.

3. The process according to claim 1 which is process for enhancing ability to learn in a puppy.

4. The process according to claim 1 which is process for enhancing ability to learn in a kitten.

5. A process for enhancing ability to learn in a puppy or kitten comprising orally administering to a respective maternal animal during nursing of the puppy or kitten a composition comprising:
   a. from about 0.02% to less than about 0.18%, by weight of the composition on a dry matter basis, therapeutically effective docosahexaenoic acid;
   b. an omega-6 fatty acid;
   c. from about 20% to about 50%, by weight of the composition on a dry matter basis, protein; and
   d. from about 5% to about 35%, by weight on a dry matter basis, fat;
   wherein the composition is a supplement selected from the group consisting of biscuits, chews, gravies, and treats or is a food composition selected from the group consisting of nutritionally balanced kibbles and semi-moist foods.

6. The process according to claim 5 wherein the composition is a supplement composition.

7. The process according to claim 5 which is process for enhancing ability to learn in a puppy.

8. The process according to claim 5 which is process for enhancing the property in a kitten.

9. A process for enhancing ability to learn in a puppy or kitten comprising orally administering to a respective maternal animal during gestation of the puppy or kitten a composition comprising:
   a. from about 0.02% to less than about 0.18%, by weight of the composition on a dry matter basis, therapeutically effective docosahexaenoic acid;
   b. an omega-6 fatty acid;
   c. from about 20% to about 50%, by weight of the composition on a dry matter basis, protein; and
   d. from about 5% to about 35%, by weight on a dry matter basis, fat; and
   wherein the composition is a supplement selected from the group consisting of biscuits, chews, gravies, and treats or is a food composition selected from the group consisting of nutritionally balanced kibbles and semi-moist foods.

10. The process according to claim 9 wherein the composition is a supplement composition.

11. The process according to claim 9 which is process for enhancing ability to learn in a puppy.

12. The process according to claim 9 which is process for enhancing ability to learn in a kitten.

13. The process according to claim 9 further comprising orally administering to the respective maternal animal the composition during nursing of the puppy or kitten.

14. The process according to claim 13 further comprising orally administering to the respective maternal animal the composition during weaning of the puppy or kitten.

15. The process according to claim 9 further comprising orally administering to the puppy or kitten the composition during weaning of the puppy or kitten.

16. The process according to claim 13 further comprising orally administering to the puppy or kitten the composition during weaning of the puppy or kitten.

17. The process according to claim 14 further comprising orally administering to the puppy or kitten the composition during weaning of the puppy or kitten.

18. The process according to claim 1 wherein the composition is a food composition.

19. The process according to claim 13 wherein the DHA sufficiency index of the puppy or kitten is greater than about 1 at 14 days of age.

20. A process for enhancing ability to learn in a puppy or kitten comprising orally administering to the puppy or kitten a food composition formulated for puppies or kittens comprising:
   a. from about 0.02% to less than about 0.18%, by weight, therapeutically effective docosahexaenoic acid;
   b. an omega-6 fatty acid;
   c. from about 20% to about 50%, by weight of the composition on a dry matter basis, protein; and
   d. from about 5% to about 35%, by weight of the composition on a dry matter basis, fat.

21. The process according to claim 20 wherein the composition further comprises on a dry matter basis, from about 20% to about 50% protein and from about 5% to about 35% fat, by weight of the composition.

22. The process according to claim 20 wherein the composition is a food composition selected from the group consisting of nutritionally balanced kibbles and semi-moist foods.

23. The process according to claim 20 wherein the composition is a supplement composition selected from the group consisting of biscuits, chews, gravies, and treats.

24. The process according to claim 20 which is process for enhancing ability to learn in a puppy.

25. The process according to claim 20 which is process for enhancing ability to learn in a kitten.

26. The process according to claim 20 wherein the composition is orally administered during at least weaning of the puppy or kitten.

27. The process according to claim 20 wherein the composition is orally administered during at least subsequent to weaning of the puppy or kitten.

28. The process of claim 1 wherein the composition is a food composition comprising about 20% to about 50% protein and from about 5% to about 35% fat.

29. The process of claim 1 wherein the composition comprises at least about 0.08% docosahexaenoic acid.

30. The process of claim 1 wherein the composition comprises at least about 0.12% docosahexaenoic acid.

31. The process of claim 5 wherein the composition is a food composition comprising about 20% to about 50% protein and from about 5% to about 35% fat.

32. The process of claim 5 wherein the composition comprises at least about 0.08% docosahexaenoic acid.

33. The process of claim 5 wherein the composition comprises at least about 0.12% docosahexaenoic acid.

* * * * *